(12) United States Patent
Botzer (10) Patent No.: US 11,944,459 B2
(45) Date of Patent: Apr. 2, 2024

(54) METHODS AND SYSTEMS FOR ESTIMATION OF RESIDUAL ECG NOISE LEVEL AND ADAPTIVE NOISE THRESHOLD

(71) Applicant: Biosense Webster (Israel) Ltd., Yokneam (IL)

(72) Inventor: Lior Botzer, Timrat (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 422 days.

(21) Appl. No.: 16/731,646

(22) Filed: Dec. 31, 2019

(65) Prior Publication Data

US 2021/0196139 A1 Jul. 1, 2021

(51) Int. Cl.
| | |
|---|---|
| A61B 5/316 | (2021.01) |
| A61B 5/00 | (2006.01) |
| A61B 5/282 | (2021.01) |
| A61B 5/287 | (2021.01) |
| A61B 5/346 | (2021.01) |

(52) U.S. Cl.
CPC ............ *A61B 5/7203* (2013.01); *A61B 5/282* (2021.01); *A61B 5/287* (2021.01); *A61B 5/346* (2021.01)

(58) Field of Classification Search
CPC ................................ A61B 5/316; A61B 5/382
USPC .................................................. 600/508–509
See application file for complete search history.

(56) References Cited

U.S. PATENT DOCUMENTS

| | | | |
|---|---|---|---|
| 5,042,499 A | 8/1991 | Frank et al. | |
| 5,265,617 A | 11/1993 | Verrier | |
| 5,704,365 A | 1/1998 | Albrecht et al. | |
| 5,810,014 A | 9/1998 | Davis | |
| 5,924,980 A | 7/1999 | Coetzee | |
| 5,983,127 A | 11/1999 | dePinto | |
| 8,543,195 B1 | 9/2013 | Brockway et al. | |
| 2010/0286532 A1 | 11/2010 | Farringdon et al. | |
| 2012/0123232 A1 | 5/2012 | Najarian et al. | |
| 2013/0190638 A1 | 7/2013 | Chon et al. | |
| 2013/0289424 A1* | 10/2013 | Brockway ............ | A61B 5/6801 |
| | | | 600/509 |

(Continued)

OTHER PUBLICATIONS

European Search Report for corresponding EPA No. 20217772.1 dated May 21, 2021.

*Primary Examiner* — Nicole F Lavert
(74) *Attorney, Agent, or Firm* — Volpe Koenig (57) ABSTRACT

A system including a means for estimating the residual noise level in electrocardiogram (ECG) signals is disclosed. The disclosed system and methods may be used in an electrocardiograph devices. According to an exemplary embodiment of the present invention, a plurality of electrodes positioned in proximity to a cardiac structure may measure an electrical signal of the cardiac structure to produce the ECG signal. The system may segment the ECG signal into a plurality of segments. For each of the plurality of segments, the linear trend energy and/or direct current (DC) energy may be removed from the segment, and the estimated noise energy of the segment may be calculated. A subset of the plurality of segments with a minimum estimated noise energy may be selected. The residual noise energy of the ECG signal may be estimated by calculating an average of the estimated noise energy over the subset of segments.

20 Claims, 6 Drawing Sheets (56) References Cited

U.S. PATENT DOCUMENTS

2014/0005988 A1* 1/2014 Brockway .............. A61B 5/349
  703/2
2015/0313484 A1* 11/2015 Burg ................... A61B 5/7257
  600/534
2019/0384757 A1* 12/2019 Garrett ................ A61B 5/7267

* cited by examiner

FIG. 3D ized signal and the noise signal. Existing methods for separating these signals tend to be very complex. Thus, there is a need for a more simplified, accurate and real-time approach to noise estimation in ECG signals, which can be used to assess and manage noise level in systems that rely on ECG.

METHODS AND SYSTEMS FOR ESTIMATION OF RESIDUAL ECG NOISE LEVEL AND ADAPTIVE NOISE THRESHOLD

FIELD OF INVENTION

The present invention relates generally to systems and methods for estimating noise levels in electrical signals, and more specifically systems and methods for estimating noise levels in electrocardiogram (ECG) signals and adaptive noise threshold algorithms.

BACKGROUND

Electrocardiography testing measures and records the electrical activity of the heart over a period of time using electrodes placed on the skin and/or inside the heart using a catheter. These electrodes detect the small electrical changes that arise from the heart muscle's electro-physiologic pattern of depolarizing during each heartbeat and thus can be used to detect abnormal cardiac conditions, such as myocardial infarction, pulmonary embolism, structural heart disease (e.g., cardiac murmur), tachycardia, or cardiac arrhythmia (e.g., atrial fibrillation). Electrocardiography may be performed by an electrocardiograph machine and the resulting testing produces an electrocardiogram (abbreviated equivalently as EKG or ECG) showing the electrical signals in the heart, typically as graph of the voltage of the heart's electrical activity over time.

During each heartbeat, a healthy heart has an orderly progression of depolarization. This orderly pattern of depolarization gives rise to the characteristic ECG tracing. To the trained clinician, the morphology of the ECG signal conveys a large amount of information about the structure of the heart and the function of its electrical conduction system. Among other things, an ECG can be used to measure the rate and rhythm of heartbeats, the size and position of the heart chambers, the presence of any damage to the muscle cells or conduction system of the heart, the effects of cardiac drugs, and the function of implanted pacemakers. Interpretation of the ECG is fundamentally about understanding the electrical conduction system of the heart. Normal conduction starts and propagates in a predictable pattern, and deviation from this pattern can be a normal variation or be pathological. Thus, the presence of noise in ECG signal can hinder the ability to effectively analyze the heart activity. Moreover, many algorithms and systems, including cardiac 3D imaging and ablation systems (e.g., the CARTO® system), rely upon ECG signals for reference, mapping and analysis. To improve the way such systems and algorithms function, accurate and real-time estimates of the actual residual noise level in an ECG signal are needed.

Electrocardiogram signals contain undesired noise, which may include low frequency noise (e.g., due to respiration and/or baseline wander) and also higher frequency noise, for example power noise and/or deflection noise. Filters (e.g., power filter) may be used to remove noise at certain frequencies. However, they may not effectively remove all noise (e.g., noise at frequencies outside the filter bandwidth). Thus, residual noise is typically present in ECG signals, even after filtering. Estimating the residual noise is important for various reasons such as monitoring system performance, and adapting various algorithms. ECG noise estimation methods, are challenged by the presence of concurrent signals and noise. Thus, an approach to noise estimation may include as a first step an attempt to separate between the desired signal and the noise signal. Existing methods for separating these signals tend to be very complex. Thus, there is a need for a more simplified, accurate and real-time approach to noise estimation in ECG signals, which can be used to assess and manage noise level in systems that rely on ECG.

SUMMARY

A system including a means for estimating the residual noise level in electrocardiogram (ECG) signals is disclosed. The disclosed system and methods may be used in an electrocardiograph device. According to an exemplary embodiment of the present invention, a plurality of electrodes positioned in proximity to a cardiac structure may measure an electrical signal of the cardiac structure to produce the ECG signal. The system may segment the ECG signal into a plurality of segments. For each of the plurality of segments, a trend including a constant direct current (DC), a linear trend and/or an interpolated low frequency trend may be removed from the segment, and the estimated noise energy of the segment may be calculated. A subset of the plurality of segments with a minimum estimated noise energy may be selected. The residual noise energy of the ECG signal may be estimated by calculating an average of the estimated noise energy over the subset of segments. The estimated noise energy may be used in a variety of applications, for example to compare and select diagnostic equipment (e.g., catheters, electrodes) with minimal noise, to detect and alert errors in equipment and for troubleshooting, and to adjust system performance and system threshold/algorithms utilizing the estimated noise in the system.

BRIEF DESCRIPTION OF THE DRAWINGS

The foregoing and other features and advantages of the disclosure will be apparent from the following, more particular description of preferred embodiments of the disclosure, as illustrated in the accompanying drawings.

DETAILED DESCRIPTION OF THE EMBODIMENTS

An exemplary electrocardiograph system may include a number of leads (e.g., twelve leads, or may be less or more) and a number of electrodes (e.g., ten electrodes, or may be more or less) placed on the patient's limbs and on the surface of the chest. The overall magnitude of the electrical potential of the heart is measured from the leads, each corresponding to a different measurement angle, and is recorded over a period of time. Electrocardiography performed with intracardiac electrodes, that are for example mounted on a catheter placed inside a chamber of the heart, produce and ECG referred to as an intracardiac electrocardiogram (ICEG), and may be utilized in combination with, or in the alternative to, the leads placed on the exterior of the patient. A lead composed of two electrodes of opposite polarity is called bipolar lead. A lead composed of a single positive electrode and a reference point is a unipolar lead.

In order to measure heart muscle electrical activity, the ECG electrodes have to be able to detect very small changes in potential energy on the patient's skin or heart tissue. For example, the electrical changes may be detected by ECG electrodes as cardiac electrical signals measuring on the order of 1 millivolt (mV) or less.

In a conventional intracardiac electrocardiograph system, an ECG electrode in contact with the skin and/or cardiac tissue measures heart signal current flowing towards the electrode as a positive charge, and heart signal current flowing away from the electrode as a negative charge, to produce a voltage reading of the heart's electrical signals over time. A goal of an electrocardiograph system is to minimize the artifacts and maximize the accuracy of the EKG signal in order to provide reliable information to the physician. ECG signals produced by electrocardiograph systems are widely used in diagnosing and monitoring cardiac conditions, they are sensitive to miscellaneous mixed noises, which may reduce the diagnostic accuracy and hinder a physician's ability to effectively diagnose and treat cardiac conditions.

According to exemplary embodiments of the present invention, the disclosed electrocardiograph systems and methods employ a dynamic and real-time residual noise estimation procedure to estimate the residual noise level in ECG signals, including body surface or intracardiac ECG signals. Moreover, the disclosed residual noise estimation procedure of the present invention may be employed with other forms of signals such as neural recordings, electrical signals over communication lines, as well as any other electrical signals where the desired signal and noise signal need to be separated in time, including signals generated in non-biomedical applications. According to an exemplary embodiment of the present invention, the residual noise estimation procedure may assume that an ECG signal contains short sections and does not contain local or far-field activity. According to the exemplary noise estimation procedure, the ECG signal is segmented into short segments (e.g., 40 to 50 millisecond windows). The direct current (DC) component, linear trend component and/or any low pass components, are removed from the ECG segments, and the energy of each ECG segment is calculated (e.g., by calculating the root-mean-square or peak-to-peak amplitude). Then, the non-DC, non-trend energy of the RMS of the ECG segment is determined and used as an estimate of noise level of the ECG signal. The present invention exploits the characteristic that the energy level of the noise does not typically change abruptly (except perhaps in the case of communication noise that is temporal). Further details of the present invention are described below.

Figure 1:
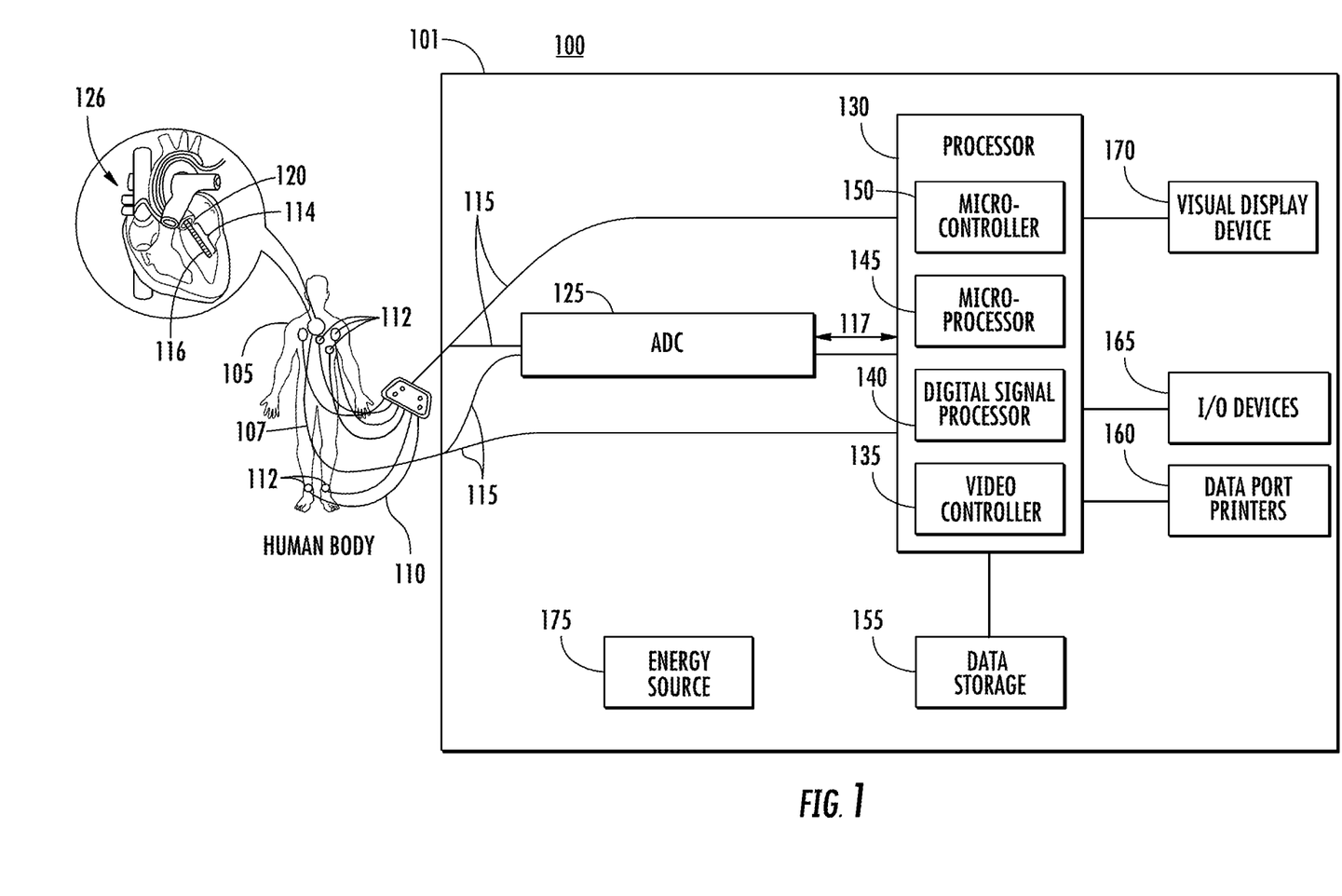
FIG. 1 is a schematic diagram of an example electrocardiograph device 100, according to an exemplary embodiment.

FIG. 1 is a schematic diagram of an example electrocardiograph device 100, according to exemplary embodiments. The electrocardiograph device 100 may include, but is not limited to include, any of the following components: console system 101; intracardiac leads 107 connected to a catheter 120 with distal end 114 inserted into the heart 126 of the patient 105; non-contact electrodes 116 located at the distal end 114 of catheter 120; and leads 110 connected to electrodes 112 positioned in various locations on the skin of the patient 105. The console system 101 may include, but is not limited to include, any of the following components: analog-to-digital converter (ADC or A/D converter) 125; processor 130; data storage 155; data port printers 160; input/output (I/O) devices 165; visual display device 170; and/or energy source device 175. The processor 130 may include, but is not limited to include, any one or more of the following components: video controller 135; digital signal processor (DSP) 140; microprocessor 145; and/or microcontroller 150.

The catheter 120, leads 107 and 110, electrodes 112 and 116, and/or other components not shown (e.g., additional catheters, sensors, a transformer, etc.) of the electrocardiograph device 100 may be used directly on, in, and/or in proximity to the patient 105 in order to gather information to be used for visualization, diagnostics, and therapy (e.g., ablation therapy). This information may be provided to the console system 101 for processing, visualization and operator control and direction, some of which is described below.

The series of leads 110 and intracardiac leads 107 connect electrodes 112 on the surface of the skin of the patient 105 and electrodes 116 on the catheter 120 inside the heart 126, respectively, to the main console 101 of the electrocardiograph device 100. In an example, intracardiac catheter 120 may be used for diagnostic and/or therapeutic treatment, such as for mapping electrical potentials in the heart 126 of the patient 105. In an example, the leads may be bipolar or unipolar. In an example, the catheter 120 may be inserted into the vascular system of the patient 105 so that the distal end 114 of the catheter 120 enters a chamber of the patient's heart 126. Although FIG. 1 shows a single catheter 120 and intracardiac lead 107, additional catheters and leads, not shown, with one or more electrodes, and/or sensors may be similarly used. Moreover, an electrocardiograph device 100 may use only surface electrodes 112, or only intracardiac electrodes 116, or both the surface electrodes 112 and intracardiac electrodes 116 for the ECG readings.

A raw ECG signal 115 (i.e., analog input signal) is acquired from any one (or more) of the electrodes 112 and/or 116 and converted from an analog to a digital format by the adjustable gain ADC 125. The ADC 125 generates and provides a digital output 117 of the ECG signal 115 by sampling the analog input signal 115 at a sampling rate. The resolution of the ADC 125 indicates the number of discrete values that the ADC 125 can produce over the range of analog values, and can be defined electrically in volts. The number of voltage intervals that the ADC 125 can produce is given by 2 m, where M is the ADC's resolution in bits.

Once the analog signal is converted, the ADC 125 communicates the digital ECG signal to the processor 130 to produce the ECG graph and/or perform other ECG analysis. Processor 130 may be coupled to data storage 155, data ports and printers 160, other I/O devices 165, and a visual display device 170, which may be used to display the ECG produced by electrocardiograph device 100. The electrocardiograph device 100 and/or any of the components therein may be powered by one or more energy sources 175.

Data storage 155 is any device that records information. Data storage may provide a storage medium for the signals included within device 100 and a place for calculations of processor 130 to be stored.

Microprocessor 145 may be a computer processor which incorporates the functions of a computer's central processing unit (CPU) on a single integrated circuit (IC), or a few integrated circuits. Microprocessor 145 may be a multipurpose, clock driven, register based, programmable electronic device which accepts digital or binary data as input, processes it according to instructions stored in its memory or data storage 155, and provides results as output. Microprocessor 145 contains both combinational logic and sequential digital logic.

Micro controller 150 may be one or more small computers on a single integrated circuit. Micro controller 150 may contain one or more CPUs along with memory and programmable input/output peripherals. Program memory in the form of Ferroelectric RAM, NOR flash or OTP ROM is also often included on chip, as well as a small amount of RAM. Microcontrollers are designed for embedded applications, in contrast to the microprocessors used in personal computers or other general purpose applications consisting of various discrete chips.

DSP 140 may perform digital signal processing to perform a wide variety of signal processing operations. The signals processed in this manner are a sequence of numbers that represent samples of a continuous variable in a domain such as time, space, or frequency. Digital signal processing can involve linear or nonlinear operations. Nonlinear signal processing is closely related to nonlinear system identification and can be implemented in the time, frequency, and spatio-temporal domains. The application of digital computation to signal processing allows for many advantages over analog processing in many applications, such as error detection and correction in transmission as well as data compression. DSP is applicable to both streaming data and static (stored) data.

Figure 2:
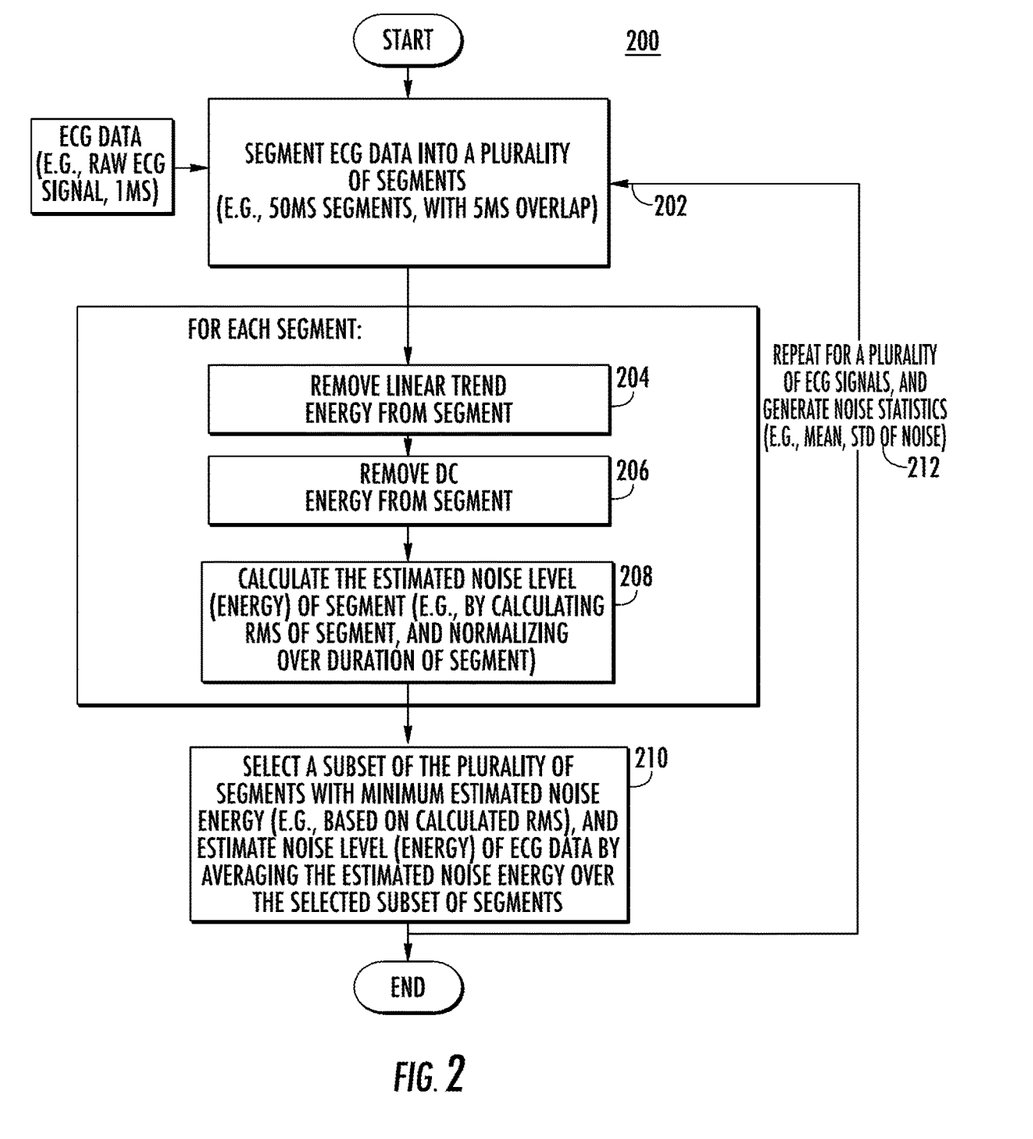
FIG. 2 is a flow diagram of an example procedure for estimating a noise level in an electrocardiogram (ECG) signal, according to an exemplary embodiment.

FIG. 2 is a flow diagram of an example residual ECG noise level estimation procedure 200, according to an exemplary embodiment of the present invention. The example residual ECG noise level estimation procedure 200 may be implemented in an electrocardiograph system, such as the example electrocardiograph device 100 of FIG. 1. For example, the residual ECG noise level estimation procedure 200 may be implemented in processor 130 and using raw ECG signal 115.

At step 202 of the residual ECG noise level estimation procedure 200 illustrated in FIG. 2, ECG data is segmented into a plurality of overlapping segments or windows. According to an exemplary embodiment, the ECG data may be a raw ECG signal (e.g., a unipolar or bipolar ECG signal) generated by one or more electrodes located in or nearby a patient's heart and prior to any noise filtering (e.g., power filtering). Procedure 200 may be performed on various versions of an ECG signal (i.e., before/after various stages of processing). According to exemplary embodiments, the ECG data may be a raw analog ECG signal before or after power filtering, or the ECG data may be a processed (e.g., CARTO) ECG signal following power filtering, high-pass filtering and/or low-pass filtering. For example, performing procedure 200 on raw analog signals prior to power filtering enables detection of the actual noise level introduced by the catheter(s)/electrode(s), which may be masked by filtering. Furthermore, in a clinical setup, other sources of noise may be introduced that the power filter is not designed to eliminate and/or the power filter may introduce other issues or cause error. In another example, procedure 200 may be performed after power filtering, for example to estimate the effectiveness of the filtering, and/or to use the resulting residual noise level estimate as a dynamic (over time) noise level estimate in systems and algorithms that take account the noise level, and/or for reporting the resulting residual noise level estimate to a monitor station (user) to be used for example for correction, analysis, and/or big data.

The duration of the segments may be chosen to isolate the energy fluctuations due to undesirable noise from the non-DC or trend energy (e.g., slope effects in the signal) due to the atrial/ventricle signals of interest. In particular, segments may be selected to be short of enough so that the non-DC trend energy is minimal. For example, most tachycardia (aside from perhaps atrial fibrillation) include long periods of no atrial/ventricle signals and thus short segments within those periods may include minimal to no trend energy. In an example, segments of approximately 40 ms-50 ms in duration may be chosen for a unipolar ECG signal of 1 second duration. Example segments are for 1 second ECG signal are shown in FIGS. 3C and 3D. According to an exemplary embodiment, adjacent segments in the plurality of segments may partially overlap in time. For example, the overlap between adjacent segments may be approximately 10% or less of the segment duration (e.g., 5 ms overlap for a 50 ms segment). According to other exemplary embodiments, the segments may not overlap, and may be adjacent or may be chosen a regularly spaced intervals.

For each of the plurality of ECG segments, one or more of the following steps (i.e., steps 204, 206, and/or 208) may be performed. At step 204 of the residual ECG noise level estimation procedure 200 illustrated in FIG. 2, linear trend energy is determined and removed from the ECG segment. The linear trend energy, corresponding to the increasing or decreasing slope of the ECG segment, may be determined using, for example, linear regression techniques. Examples of trend energy include the sharp slopes or spikes in the ECG signal such as the spikes near or around 0.1 second and 0.6 second in FIGS. 3C and 3D.

In an example, the linear trend energy may be determined using regression analysis to find an equation (e.g., in the form of $Y=\mu X+\beta$) that fits the straight line (or linear) trend of the data in the ECG segment. Once the linear trend energy is determined, it may be subtracted from the ECG segment in order to remove the linear trend energy. In some cases, the linear trend energy may be minimal or non-existent within a short ECG segment (even if there is a trend present over a window of time that is larger than the segment, for example the entire duration of the signal being measured). Thus, in such cases step 204 may be omitted.

At step 206 of the residual ECG noise level estimation procedure 200 illustrated in FIG. 2, DC energy and/or any low pass energy components are removed from the ECG segment. The DC energy (and any low pass energy components), also referred to as the DC bias, DC component, DC offset or DC coefficient, is determined and calculated as the mean amplitude of the waveform of the ECG segment, which may then be subtracted from the ECG segment to remove the DC component.

At step 208 of the residual ECG noise level estimation procedure 200 illustrated in FIG. 2, the estimated magnitude of the noise level (i.e., the estimated noise energy) is calculated, for example by taking the root-mean-square (RMS) amplitude (RMS of alternating current (AC) voltage)

or peak-to-peak (PP) amplitude of the ECG segment (with the liner trend/low-pass/DC energy removed). When calculating the estimated noise energy, the estimated noise energy value (e.g., RMS or PP amplitude value) may be normalized by the duration of segment (or energy window). According to other exemplary embodiments, any known estimation techniques may be used to calculate the estimated noise level of the segment, including, but not limited spectral density estimation techniques.

Once the estimated noise level of each of the plurality of ECG segments of the ECG data is calculated, then at step 210 of the residual ECG noise level estimation procedure 200 illustrated in FIG. 2, a subset (e.g., one or more) of the plurality of ECG segments is selected based on the ECG segments with the minimum estimated noise level (e.g., the minimum RMS or PP amplitude), and the estimated average noise level of the ECG data is calculated by taking the average of the estimated noise levels of the selected subset of ECG segments. The noise estimate is preferably averaged over multiple segments to provide a more reliable estimate. The average of the estimated noise levels of the selected subset of ECG segments may be a simple average or a weighted average. For example, the weighted average may take into consideration previous noise estimates to determine weights, and/or the consistency of the noise estimate values over time (e.g., if the noise estimate value changes abruptly from a 1 second signal to the next 1 second signal, there may be noise or error in the estimation). According to an exemplary embodiment, a subset of the plurality of segments (one or more) are used (e.g., 3 segments). In another exemplary embodiment, the noise estimate may be averaged over all segments of the original ECG data signal. In an alternate exemplary embodiment, only one estimated noise level (e.g., the minimum noise level) is used and the average is not taken.

According to an exemplary embodiment of the present invention, the noise energy of ECG segments with the minimum noise energy is preferably used for estimating the noise energy of the ECG data. However, according to alternate exemplary embodiments, other noise energy estimates that are not the lowest valued may be used, such as a sampling of noise energy estimates in the lowest 10% percentile.

Optionally, at step 212 of the residual ECG noise level estimation procedure 200 illustrated in FIG. 2, the steps for calculating the estimated average noise level (e.g., steps 202-210) may be repeated for plurality of ECG data (e.g., X ECG signals of 1 second duration each, or equivalently a longer ECG signal of X seconds divided into 1 second signals), and noise statistics such as mean and standard deviation of noise may be generated over the plurality of ECG signals. According to an exemplary embodiment, ECG segments of electrical activity where noise should not be measured can be marked or flagged. For example, if the system knows that a special condition is occurring at a particular time, the system can temporarily ignore or pause the noise level estimation procedure calculation (e.g., during ablation or during specific signal periods such as during detection of ventricle far field during atrial mapping).

The estimated noise energy of the ECG data generated at step 210 may be provided to and used by systems or algorithms, or directly to the user for analysis or troubleshooting, in a variety of applications. Some examples of applications and uses of the estimated noise level of ECG signals generated using the residual ECG noise level estimation procedure 200 illustrated in FIG. 2 are described below.

According to an exemplary embodiment of the present invention, an electrocardiography system may be combined with other medical systems, such as real-time 3D cardiac imaging system for visualizing heart activity and defects, and/or cardiac ablation systems for correcting heart rhythm defects, known as arrhythmias, by creating lesions to destroy tissue in the heart that contributes to the rhythm defects. An example of a real-time 3D imaging system for cardiac ablation is the CARTO® 3 System, produced by Biosense Webster®, Inc., a subsidiary of Johnson & Johnson. The CARTO® 3 System uses electromagnetic technology to create 3D maps of a patient's cardiac structure, show the exact location and orientation of the catheters in the heart and provide the ECG of the electrical signals in the heart at the respective locations. In some applications, different catheters may be used with the CARTO® 3 System, and the residual ECG noise level estimation procedure 200 illustrated in FIG. 2 may be used to compare the noise performance between different catheters CARTO® 3 System. The following examples compare a few points that were collected with different catheters on a same site in a cardiac chamber and under similar arrhythmia conditions. Signals were extracted to visualize the ECG signals in their raw form (without any filtering), raw form after power filtering (but without high-pass and/or low-pass filtering) and processed form (with power filtering, high-pass filtering and low-pass filtering). Further examples of filters (in addition to power filters) that may be used to process ECG signals prior to ECG noise energy estimation include, but are not limited to include, linear regression median filters, derivative filters, and/or high pas filter (e.g., to remove baseline wandering prior to ECG noise energy estimation).

Figure 3A:
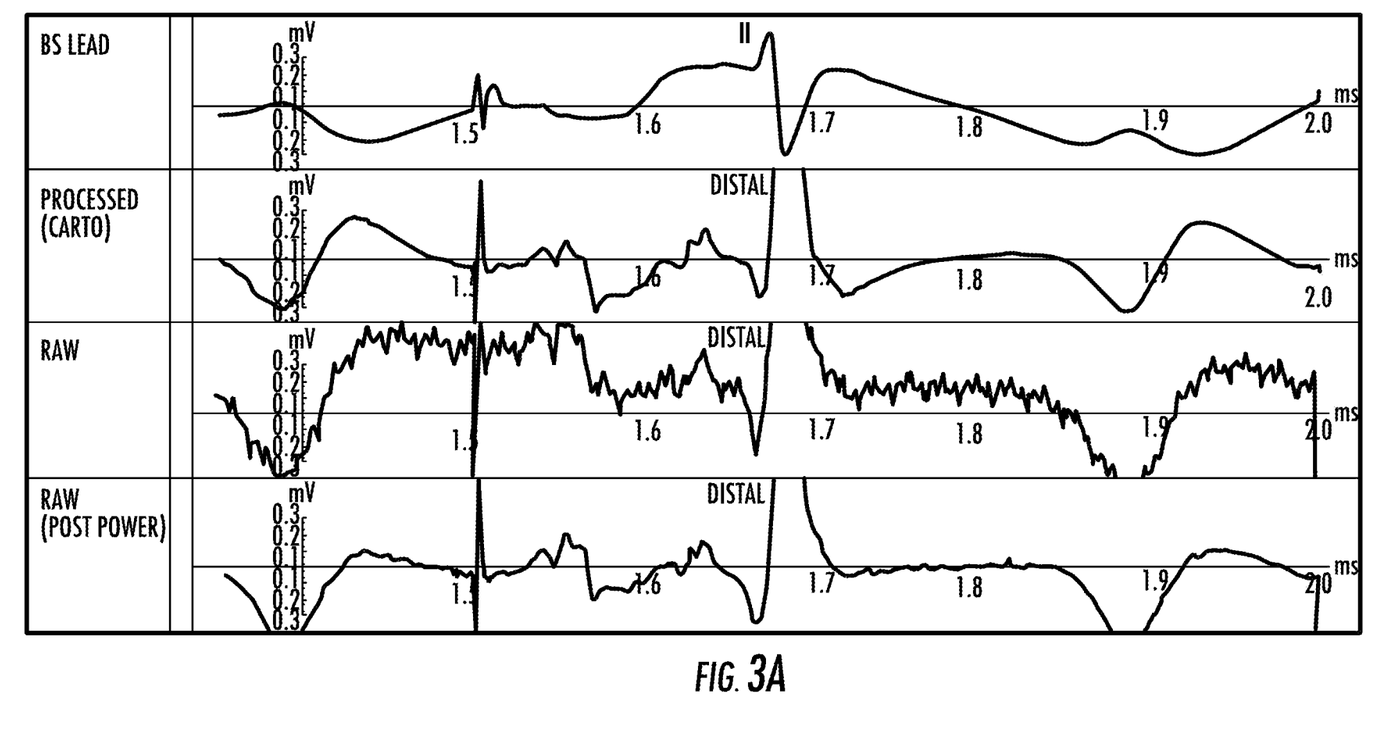
FIG. 3A illustrates an example ECG noise level at different levels of an ECG signal produced using a first type of catheter in a CARTO system, where the ECG signal is shown in raw form (digital output), after power noise filtering, and after user selectable filtering (by the CARTO system)
Figure 3B:
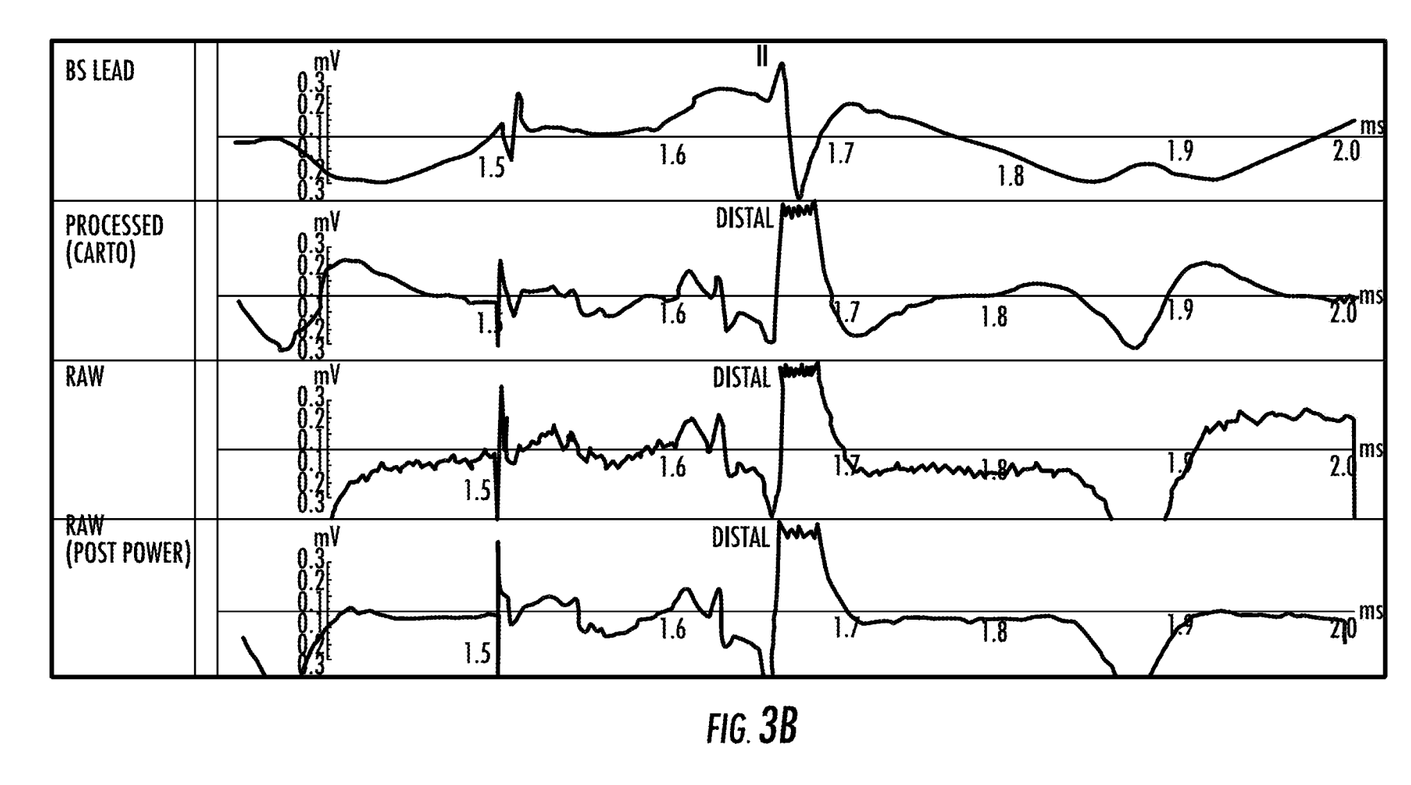
FIG. 3B illustrates an example ECG noise level at different levels of an ECG signal produced using a second type of catheter in a CARTO system, where the ECG signal is shown in raw form (digital output), after power noise filtering, and after user selectable filtering (by the CARTO system)
Figure 3C:
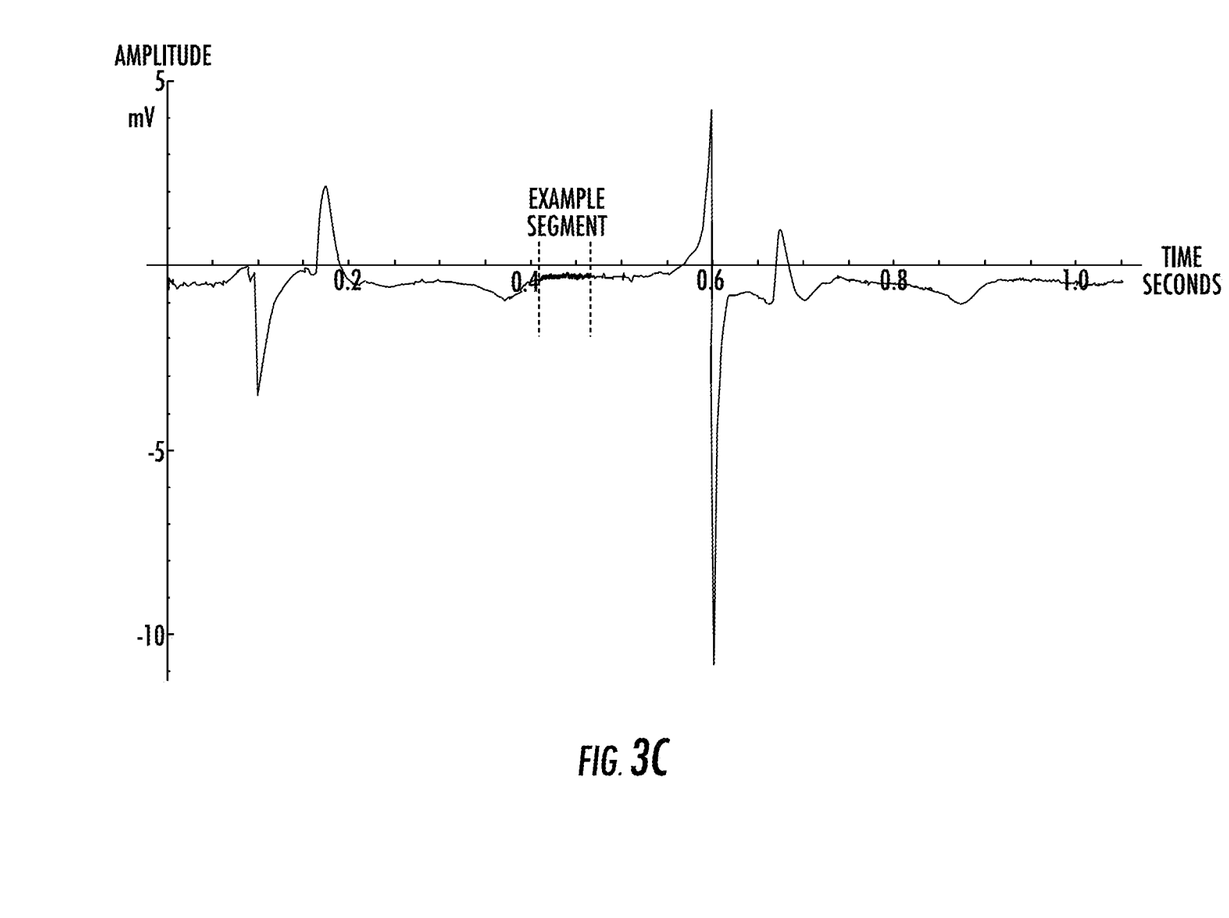
FIG. 3C illustrates an example one second ECG signal in raw format produced using the first type of catheter in the CARTO system, and shows an example segment used to calculate the residual ECG noise level estimate according to the procedure illustrated in FIG. 2.
Figure 3D:
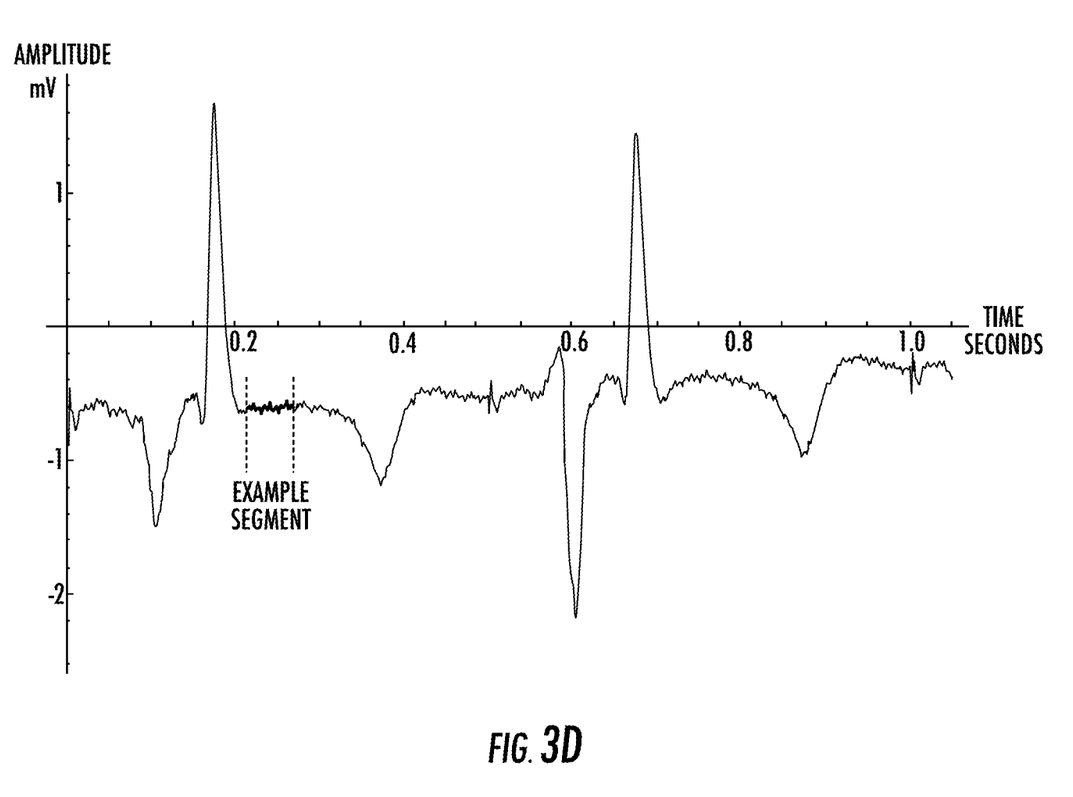
FIG. 3D illustrates an example one second ECG signal in raw format produced using the second type of catheter in the CARTO system, and shows an example segment used to calculate the residual ECG noise level estimate according to the procedure illustrated in FIG. 2.

FIGS. 3A and 3B illustrate examples of different levels of an ECG signal produced using a first type of catheter and a second type of catheter, respectively, in a CARTO system.

FIG. 3A shows an example distal unipolar ECG signal taken from a low voltage point (0.2 mV) from the inferior posterior view of the right atrial (RA) cardiac chamber using the first type of catheter, and FIG. 3B shows an example distal unipolar ECG signal taken from a low voltage point (0.2 mV) from the inferior posterior view of the RA cardiac chamber using a second type of catheter. Both FIGS. 3A and 3B illustrate the ECG signals in their raw form (without any filtering), raw form post power filtering, and processed form (CARTO signal with power filtering, high-pass filtering and low-pass filtering). The residual ECG noise level estimation procedure 200 described in FIG. 2 can be applied to any of the signals in FIGS. 3A and 3B to compare the noise performance of the two different types of catheters. In th example of FIGS. 3A and 3B, it can be observed that the ECG noise levels in the CARTO system in the processed (CARTO) signals using either catheter appears to be almost identical (i.e., the difference in the signal pattern in FIG. 3A versus FIG. 3B is minimal). Thus, a meaningful analysis of the noise levels cannot be assessed based on the processed CARTO signals. However, the ECG noise levels observed in the raw ECG signals are different between the two catheters.

FIG. 3C illustrates an example one second (unipolar) ECG signal in raw format produced using the first type of catheter in the CARTO system, and shows one example segment used to calculate the residual ECG noise level estimate according to the procedure illustrated in FIG. 2. Similarly, FIG. 3D illustrates an example one second (unipolar) ECG signal in raw format produced using the second type of catheter in the CARTO system, and shows one example segment used to calculate the residual ECG noise level estimate according to the procedure illustrated in FIG.

2. In both FIGS. 3C and 3D, quieter segments are shown with less trend/DC/low-pass energy and are approximately 50 ms in duration. According to the residual ECG noise level estimation procedure 200 illustrated in FIG. 2, any short duration segment may be used by applying techniques described herein to remove any trend/DC/low-pass energy to isolate the noise energy.

In an example application of the residual ECG noise level estimation procedure 200 illustrated in FIG. 2 to segments of the raw ECG signals in FIGS. 3C and 3D (which may be averaged over multiple one second ECG signals, for example 300 one second ECG signals), it can be determined that the noise level in the raw ECG signal produced by the first type of catheter (FIG. 3C) is on the order of 57 µV, which is more than two times greater than the noise level in the raw ECG signal produced by the second type of catheter (FIG. 3D), which is approximately 21 µV. Spectrum analysis comparing the two raw signals also supports this finding, showing that the higher noise level is attributed to power harmonics.

Thus, the ECG signal comparisons for the different catheters based on residual ECG noise level estimates shows that although the processed signals appear to be the equivalent, the raw signal shown in FIG. 3A is noisier than the raw signal in FIG. 3B. This type of analysis is useful, for example in process production control to determine than the first type of catheter has inferior noise performance to the second type of catheter and for determining which type of catheter to use in different applications. As explained above, analysis based on ECG noise level estimates can be done for various levels of the signals, including signals in raw form, post power filtering or following any user selectable filtering.

According to exemplary embodiments, the residual ECG noise level estimation procedure of the present invention may be used to estimate the noise energy level in systems involving one or more intracardiac, unipolar ECG signals sensitive to noise at different frequencies, as well as algorithms designed to analyze the unipolar ECG signals. According to an exemplary embodiment, the noise level may be estimated for each catheter (where more than one catheter is used), and the catheters may be compared in terms of their corresponding estimated noise levels. According to another exemplary embodiment, the noise level may be estimated and compared for different levels of ECG outputs (e.g., in raw form, power filtered form or after user selectable filters).

According to another exemplary embodiment, the estimated noise level of ECG signals generated using the residual ECG noise level estimation procedure 200 illustrated in FIG. 2 may be used to dynamically modify a specific algorithm. For example, a mapping algorithm for detected signals in the presence of noise (e.g., Wavefront and Finder algorithms) may make use of the real-time estimated noise level to dynamically change the detection threshold of the mapping signals, thus enabling detection of low (amplitude) signals when noise level is low and increasing the detection threshold of signals when the noise is high.

According to another exemplary embodiment, the estimated noise level of ECG signals generated using the residual ECG noise level estimation procedure 200 illustrated in FIG. 2 may be used to compare the instant noise level estimate to the history of noise level estimates collected for a given system (e.g., CARTO system). For example, the comparison of estimate noise levels over time may be used to monitor the power filter algorithm performance and provide an alert to the system or user when the power filter malfunctions. More generally, the comparison of estimate noise levels over time may be used to raise an alert to the system or user about identified issues and assist in troubleshooting (e.g., comparing the noise level using different cables to identify a faulty cable).

According to another exemplary embodiment, the estimated noise level of ECG signals generated using the residual ECG noise level estimation procedure 200 illustrated in FIG. 2 may be used during production of equipment (e.g., catheters) to test the equipment during production to make sure that the design and connectivity is appropriate. According to another exemplary embodiment, the estimated noise level of ECG signals generated using the residual ECG noise level estimation procedure 200 illustrated in FIG. 2 may be used when collecting big data from a group of systems to determine which components, systems and/or conditions generate noise, and/or to verify that there is no reduction in performance due to system changes including software upgrades.

Many variations are possible based on the disclosure herein. Although features and elements are described above in particular combinations, each feature or element can be used alone without the other features and elements or in various combinations with or without other features and elements.

The systems and procedures described herein may be implemented in hardware, and/or software. A computer-based system for performing electrocardiography may be capable of running software modules that introduce additional features including the procedures described herein. The procedures described herein may enable advanced cardiac visualization, and diagnostic capabilities to enhance clinicians' ability to diagnose and treat heart rhythm disorders. Although the procedures disclosed herein are describe with respect to electrocardiography procedures within the heart, the devices and procedures may be similarly used for electrophysiology procedures in other parts of the body, such as, but not limited to, electroencephalography in the brain, electrooculography in the eye, and electropneumography in the lungs. Moreover, the procedures disclosed herein can be used to estimate the noise energy in any electrical signal, including non-biomedical electrical signals.

The methods provided may include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be mask works that are then used in a semiconductor manufacturing process to manufacture a processor which implements the methods described herein.

The methods or flow charts provided herein may be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A system for estimating residual noise energy of an electrocardiogram (ECG) signal, the system comprising:
    a plurality of electrodes configured to measure an electrical signal of a cardiac structure to produce the ECG signal; and
    a processor configured to:
    determine a segment duration based on a linear trend energy of the ECG signal, wherein the linear trend energy corresponds to an increasing or decreasing slope of the ECG signal;
    segment the ECG signal into a plurality of segments in accordance with the determined segment duration;
    for each of the plurality of segments:
        remove the linear trend energy and direct current (DC) energy from the segment, and calculate an estimated noise energy of the segment;
    select a subset of the plurality of segments with a minimum estimated noise energy;
    estimate the residual noise energy of the ECG signal by calculating an average of the estimated noise energy over the subset of segments; manage a noise level of the ECG signal using the estimated residual noise energy of the ECG signal; and enable a clinician's ability to diagnose and treat a heart disorder according to the subset of segments.

2. The system of claim 1, wherein the plurality of electrodes include at least one of intracardiac electrodes mounted on a catheter configured for insertion into a chamber of the cardiac structure and surface electrodes located on a body surface exterior to the cardiac structure.

3. The system of claim 1, wherein adjacent segments in the plurality of segments partially overlap in time.

4. The system of claim 1, wherein the ECG signal is a raw unipolar or bipolar ECG signal prior to any filtering.

5. The system of claim 1, further comprising:
    at least one power filter configured to filter the ECG signal.

6. The system of claim 1, further comprising:
    at least one of a near regression median filter, a derivative filter, or a high pass filter to filter the ECG signal.

7. The system of claim 1, wherein:
    the processor is configured to determine the segment duration so that the linear trend energy of the ECG signal is minimal.

8. The system of claim 1, wherein:
    the processor is configured to calculate the estimated noise energy of the segment by taking a root-mean-square (RMS) amplitude or peak-to-peak (PP) amplitude of the segment.

9. The system of claim 1, wherein:
    the processor is further configured to normalize the estimated noise energy of the segment by a duration of the segment.

10. The system of claim 1, wherein:
    the plurality of electrodes are further configured to produce a plurality of ECG signals; and
    the processor is configured to estimate the residual noise energy of each of the plurality of ECG signals and generate noise statistics over the plurality of ECG signals.

11. A method for estimating residual noise energy of an electrocardiogram (ECG) signal, the method comprising:
    measuring, using a plurality of electrodes, an electrical signal of a cardiac structure to produce the ECG signal;
    determining a segment duration based on a linear trend energy of the ECG signal, wherein the linear trend energy corres ponds to an increasing or decreasing slope of the ECG signal;
    segmenting the ECG signal into a plurality of segments in accordance with the determined segment duration;
    for each of the plurality of segments, removing the linear trend energy and direct current (DC) energy from the segment, and calculating an estimated noise energy of the segment;
    selecting a subset of the plurality of segments with a minimum estimated noise energy; estimating the residual noise energy of the ECG signal by calculating an average of the estimated noise energy over the subset of segments; managing a noise level of the ECG signal using the estimated residual noise energy of the ECG signal; and enabling a clinician's ability to diagnose and treat a heart disorder according to the selecting the subset of segments.

12. The method of claim 11, wherein the plurality of electrodes include at least one of intracardiac electrodes mounted on a catheter configured for insertion into a chamber of the cardiac structure and surface electrodes located on a body surface exterior to the cardiac structure.

13. The method of claim 11, wherein adjacent segments in the plurality of segments partially overlap in time.

14. The method of claim 11, wherein the ECG signal is a raw unipolar or bipolar ECG signal prior to any filtering.

15. The method of claim 11, further comprising:
    using a power filter to filter the ECG signal.

16. The method of claim 11, further comprising:
    comprising using at least one of a near regression median filter, a derivative filter, or a high pass filter to filter the ECG signal.

17. The method of claim 11,
wherein the segment duration is determined so that the linear trend energy of the ECG signal is minimal.

18. The method of claim 11, wherein:
    the estimated noise energy of the segment is calculated by taking a root-mean-square (RMS) amplitude or peak-to-peak (PP) amplitude of the segment.

19. The method of claim 11, further comprising:
    normalizing the estimated noise energy of the segment by a duration of the segment.

20. The method of claim 11, further comprising:
    producing a plurality of ECG signals;
    estimating the residual noise energy of each of the plurality of ECG signals; and
    generating noise statistics over the plurality of ECG signals.

* * * * *

UNITED STATES PATENT AND TRADEMARK OFFICE
CERTIFICATE OF CORRECTION

PATENT NO. : 11,944,459 B2
APPLICATION NO. : 16/731646
DATED : April 2, 2024
INVENTOR(S) : Lior Botzer It is certified that error appears in the above-identified patent and that said Letters Patent is hereby corrected as shown below:

In the Specification

In Column 3, Line 16, delete "and" and insert -- an --, therefor.

In Column 4, Line 61, delete "2 m," and insert -- 2M, --, therefor.

In Column 5, Line 18, delete "Micro controller" and insert -- Microcontroller --, therefor.

In Column 5, Line 19, delete "Micro controller" and insert -- Microcontroller --, therefor.

In Column 6, Line 23, delete "are for" and insert -- for --, therefor.

In Column 8, Line 31, delete "high pas" and insert -- high pass --, therefor.

In Column 8, Line 49, delete "In th" and insert -- In the --, therefor.

In Column 9, Line 26, delete "than" and insert -- whether --, therefor.

In Column 9, Line 65, delete "estimate" and insert -- estimated --, therefor.

In Column 10, Line 2, delete "estimate" and insert -- estimated --, therefor.

In Column 10, Line 34, delete "describe" and insert -- described --, therefor.

In the Claims

In Column 12, Line 11, in Claim 11, delete "corres ponds" and insert -- corresponds --, therefor.

In Column 12, Line 41, in Claim 16, delete "comprising using" and insert -- using --, therefor.

Signed and Sealed this
Seventeenth Day of September, 2024

Katherine Kelly Vidal
*Director of the United States Patent and Trademark Office*